US00PP14670P29

(12) United States Plant Patent
Hoogendoorn

(10) Patent No.: US PP14,670 P2
(45) Date of Patent: Apr. 6, 2004

(54) ALSTROEMERIA PLANT NAMED 'ZAPRIBEL'

(50) Latin Name: *Alstromeria hybrida*
Varietal Denomination: Zapribel

(75) Inventor: Cornelis Arie Hoogendoorn, Rijsenhout (NL)

(73) Assignee: Van Zanten Plants B.V., Hillegom (NL)

( * ) Notice: Subject to any disclaimer, the term of this patent is extended or adjusted under 35 U.S.C. 154(b) by 0 days.

(21) Appl. No.: 10/437,951

(22) Filed: May 13, 2003

(51) Int. Cl.[7] ..... A01H 5/00
(52) U.S. Cl. ..... Plt./309
(58) Field of Search ..... Plt./309

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Alstroemeria plant named 'Zapribel', characterized by its compact, upright and outwardly spreading growth habit, orange and yellow bi-colored flowers with dark purple-colored spots and stripes; and excellent postproduction longevity.

1 Drawing Sheet

Botanical classification/cultivar designation: Alstroemeria hybrida cultivar Zapribel.

BACKGROUND OF THE INVENTION

The present Invention relates to a new and distinct cultivar of Alstroemeria plant, botanically known as Alstroemeria hybrida, commercially used as a pot-type flowering Alstroemeria, and hereinafter referred to by the name 'Zapribel'.

The new Alstroemeria is a product of a planned breeding program conducted by the Inventor in Rijsenhout, The Netherlands. The objective of the breeding program was to develop new compact container Alstroemeria cultivars with desirable flower and plant qualities, attractive flower colors and excellent postproduction longevity.

The new Alstroemeria originated from a cross made by the Inventor in 1999 in Rijsenhout, The Netherlands, of a proprietary Alstroemeria hybrida selection identified as 88D1240-2, not patented, as the female, or seed, parent with a proprietary Alstroemeria hybrida selection identified as 96F82-2, not patented, as the male, or pollen, parent. The new Alstroemeria was discovered and selected by the Inventor as a flowering plant within the progeny of the stated cross in a controlled environment in Rijsenhout, The Netherlands in May, 2000.

Asexual reproduction of the new cultivar by root divisions taken in a controlled environment in Rijsenhout, The Netherlands, since May, 2000, has shown that the unique features of this new Alstroemeria are stable and reproduced true to type in successive generations of asexual propagation.

SUMMARY OF THE INVENTION

Plants of the cultivar Zapribel have not been observed under all possible environmental conditions. The phenotype may vary somewhat with variations in environment such as temperature and light intensity without, however, any variance in genotype.

The following traits have been repeatedly observed and are determined to be the unique characteristics of 'Zapribel'.

These characteristics in combination distinguish 'Zapribel' as a new and distinct cultivar:

1. Compact, upright and outwardly spreading plant habit.
2. Orange and yellow bi-colored flowers with dark purple-colored spots and stripes.
3. Excellent postproduction longevity.

Plants of the new Alstroemeria can be compared to plants of the parent selections. Plants of the new Alstroemeria differ from plants of the female parent selection in flower coloration as plants of the female parent selection have purple-colored flowers. Plants of the new Alstroemeria differ from plants of the male parent selection in plant size as plants of the male parent selection are taller than plants of the new Alstroemeria.

Plants of the new Alstroemeria can be compared to plants of the cultivar Staprilene, disclosed in U.S. Plant Pat. No. 11,683. In side-by-side comparisons conducted in Rijsenhout, The Netherlands, plants of the new Alstroemeria differed from plants of the cultivar Staprilene in the following characteristics:

1. Plants of the new Alstroemeria had shorter lateral branches than plants of the cultivar Staprilene.
2. Plants of the new Alstroemeria had smaller leaves than plants of the cultivar Staprilene.
3. Plants of the new Alstroemeria had shorter inflorescences than plants of the cultivar Staprilene.
4. Plants of the new Alstroemeria had orange and yellow bi-colored flowers whereas plants of the cultivar Staprilene had yellow and white bi-colored flowers.

BRIEF DESCRIPTION OF THE PHOTOGRAPH

The accompanying colored photograph illustrates the overall appearance of the new Alstroemeria, showing the colors as true as it is reasonably possible to obtain in colored reproductions of this type. Colors in the photograph may differ slightly from the color values cited in the detailed botanical description which accurately describe the colors of the new Alstroemeria. The photograph comprises a side perspective view of a typical flowering plant of 'Zapribel'.

DETAILED BOTANICAL DESCRIPTION

The aforementioned photograph, following observations and measurements describe plants of the new Alstroemeria grown in Rijsenhout, The Netherlands in a glass-covered greenhouse in 17-cm containers. During the production of the plants, day temperatures ranged from 15 to 25° C. and night temperatures ranged from 10 to 15° C. Plants used for the photograph and description were about four months old. The photograph and the description were taken during August and September, 2002. Color references are made to The Royal Horticultural Society Colour Chart, 1995 Edition, except where general terms of ordinary dictionary significance are used.

Botanical classification: Alstroemeria hybrida cultivar Zapribel.

Parentage:

*Female parent.*—Proprietary Alstroemeria hybrida selection identified as 88D1240-2, not patented.

*Male parent.*—Proprietary selection of Alstroemeria hybrida identified as 96F82-2, not patented.

Propagation:

*Type.*—By root divisions.

*Root description.*—Fibrous, fleshy, thick; white, close to 155D, in color.

*Rooting habit.*—Freely branching.

*Rhizomes.*—Shape: Elongate; rounded. Length: About 10 to 30 cm. Diameter: About 3 to 10 mm. Texture: Smooth. Color: Close to 155D.

Plant description:

*Plant habit.*—Upright, outwardly spreading and compact plant habit; freely branching, about 10 to 15 lateral branches per plant; bushy appearance.

*Time from planting to flowering.*—About 80 to 90 days.

*Plant height.*—About 25 to 35 cm.

*Plant diameter* (*spread*).—About 40 to 50 cm.

*Lateral branch description.*—Aspect: Mostly erect. Length: About 25 to 30 cm. Diameter: About 3 to 5 mm. Internode length: About 5 to 18 mm. Strength: Strong. Texture: Smooth, glabrous. Color: Close to 144B.

*Foliage description.*—Leaves asymmetrical; sessile. Length: About 6 to 7 cm. Width: About 1.4 to 1.8 cm. Shape: Lanceolate. Apex: Acute. Base: Attenuate. Margin: Entire. Texture, upper and lower surfaces: Smooth; glabrous. Venation pattern: Parallel. Color: Young and fully developed foliage, upper surface: Close to 137A; slightly glossy. Young and fully developed foliage, lower surface: Close to 137C. Venation: Upper surface: Close to 137A. Lower surface: Close to 137C.

Flower description:

*Flower type and habit.*—Single cup-shaped flowers arranged in compound umbels with about 4 to 16 flowers per umbel. Perianth segments separate. Freely and continuously flowering. Flowers not persistent.

*Natural flowering season.*—Flowering continuous during the spring in The Netherlands.

*Fragrance.*—None detected.

*Keeping quality.*—Plants will stay in flower and maintain good flower substance for about three months.

*Flower longevity on the plant.*—About four weeks.

*Flower longevity as a cut flower.*—About 18 to 20 days.

*Flower buds* (*showing color*).—Length: About 3.5 to 4 cm. Diameter: About 1.3 to 1.7 cm. Shape: Roughly ovoid. Color: Close to 172A.

*Umbel height.*—About 8 to 10 cm.

*Umbel diameter.*—About 12 to 14 cm.

*Flower height.*—About 6 to 7 cm.

*Flower diameter.*—About 5.5 to 6.5 cm.

*Flower depth.*—About 6 cm.

*Perianth.*—Arrangement: Six arranged in two whorls, each whorl with two lateral and one median segments. Size: Inner perianth: Length: Laterals, about 6 to 6.5 cm; median, 5 to 5.5 cm. Width: Laterals, about 1.8 to 2 cm; median, about 1.8 to 2 cm. Outer perianth: Length: Laterals, about 5.5 to 6 cm; median, about 5.5 to 6.5 cm. Width: Laterals, about 2.7 to 3.5 cm; median, about 3 to 3.5 cm. Shape: Inner perianth, all segments: Oblanceolate. Outer perianth, all segments: Obovate. Apex: Inner perianth, all segments: Wishbone-shaped. Outer perianth, all segments: Bracket-shaped. Base, inner and outer perianths, all segments: Attenuate. Margin, inner and outer perianths, all segments: Entire; moderately undulate. Texture, inner and outer perianths, all segments: Smooth, glabrous; velvety. Color: Inner perianth, when opening and fully opened, upper surface: Laterals: Towards apex, 32A; mid-section and base, close to 15A; spots and stripes, close to 187A. Median: 32B; spots and stripes, close to 187A. Inner perianth, when opening and fully opened, lower surface: Laterals: Towards apex, 32A; mid-section and base, close to 15A. Median: 32B. Outer perianth, when opening and fully opened, upper and lower surfaces, laterals and median: Close to 42B; towards apex, close to 30C.

*Pedicels.*—Length: About 1.5 to 2.5 cm. Diameter: About 2 to 3 mm. Strength: Strong. Angle: About 30 to 60° from vertical. Texture: Smooth, glabrous. Color: Close to 144A.

*Reproductive organs.*—Stamens: Quantity per flower: Six. Anther shape: Elliptical. Anther length: About 6 mm. Anther diameter: About 3 mm. Anther color: Close to 167A. Pollen amount: Scarce. Pollen color: Close to 202B. Pistils: Quantity per flower: One. Style length: About 4 to 5 cm. Stigma color: Orange. Ovary color: Close to 144B.

*Fruit.*—Amount: Scarce. Shape: Globular. Color: Brown.

Disease/pest resistance: Plants of the new Alstroemeria have not been observed to be resistant to pathogens and pests common to Alstroemerias.

Temperature tolerance: Plants of the new Alstroemeria have been observed to tolerate temperatures from −5 to 40° C.

It is claimed:

1. A new and distinct cultivar of Alstroemeria plant named 'Zapribel', as illustrated and described.

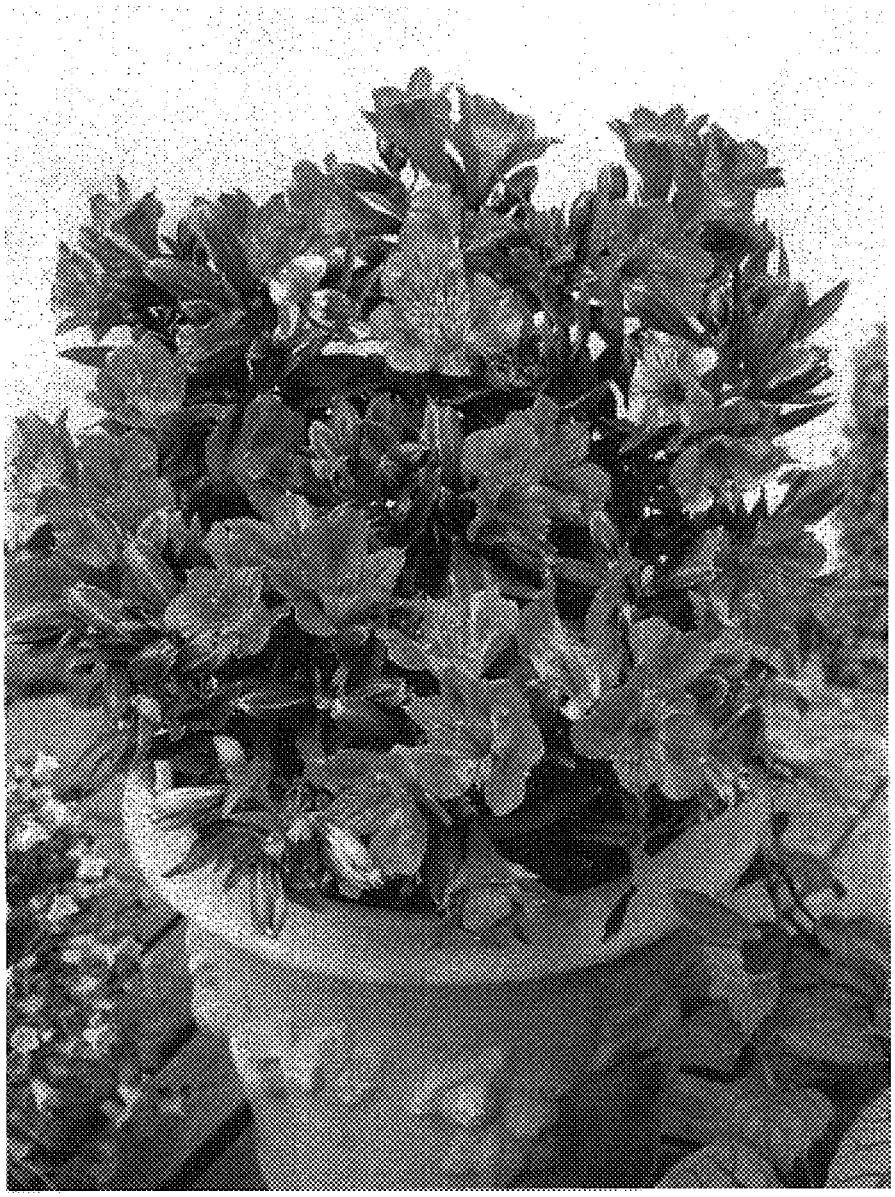

* * * * *